US007555437B2

(12) United States Patent
Pierce

(10) Patent No.: US 7,555,437 B2
(45) Date of Patent: Jun. 30, 2009

(54) MEDICAL DOCUMENTATION SYSTEM

(75) Inventor: D. Shannon Pierce, Greenville, SC (US)

(73) Assignee: Care Cam Innovations, LLC, Greenville, SC (US)

( * ) Notice: Subject to any disclaimer, the term of this patent is extended or adjusted under 35 U.S.C. 154(b) by 112 days.

(21) Appl. No.: 11/452,707

(22) Filed: Jun. 14, 2006

(65) Prior Publication Data
US 2007/0294105 A1 Dec. 20, 2007

(51) Int. Cl.
G06Q 10/00 (2006.01)
G06Q 50/00 (2006.01)

(52) U.S. Cl. ............................................. 705/2; 705/3
(58) Field of Classification Search ................ 705/2, 705/3
See application file for complete search history.

(56) References Cited

U.S. PATENT DOCUMENTS

| | | | | | |
|---|---|---|---|---|---|
| 4,835,372 | A | * | 5/1989 | Gombrich et al. | 235/375 |
| 5,494,046 | A | * | 2/1996 | Cross | 600/595 |
| 5,847,305 | A | * | 12/1998 | Yoshikawa et al. | 84/634 |
| 5,867,821 | A | | 2/1999 | Ballantyne et al. | |
| 5,877,742 | A | * | 3/1999 | Klink | 345/685 |
| 6,031,526 | A | | 2/2000 | Shipp | |
| 6,202,060 | B1 | | 3/2001 | Tran | |
| 6,779,024 | B2 | * | 8/2004 | DeLaHuerga | 709/217 |
| 2002/0005894 | A1 | * | 1/2002 | Foodman et al. | 348/143 |
| 2002/0068556 | A1 | * | 6/2002 | Brown | 455/420 |
| 2002/0077841 | A1 | | 6/2002 | Thompson | |
| 2003/0020611 | A1 | * | 1/2003 | Script et al. | 340/568.1 |
| 2003/0046090 | A1 | * | 3/2003 | Brown | 705/1 |
| 2003/0115082 | A1 | | 6/2003 | Jacobson et al. | |
| 2003/0228033 | A1 | * | 12/2003 | Daniel et al. | 382/104 |
| 2004/0078215 | A1 | | 4/2004 | Dahlin et al. | |
| 2004/0100376 | A1 | * | 5/2004 | Lye et al. | 340/539.12 |
| 2004/0114054 | A1 | * | 6/2004 | Mansfield et al. | 348/700 |
| 2005/0027567 | A1 | | 2/2005 | Taha | |
| 2005/0038326 | A1 | | 2/2005 | Mathur | |

OTHER PUBLICATIONS

Dick Tracy Watch, picture.*
NBA Western Conference Finals, Game 6, http://reneponce.com/lakers053104/lakers053104.html.*

(Continued)

Primary Examiner—C. Luke Gilligan
Assistant Examiner—Neal R Sereboff
(74) Attorney, Agent, or Firm—Smith Moore Leatherwood LLP; Thomas W. Epting

(57) ABSTRACT

An electronic documentation system for use in care for a patient given by a health care provider, comprising a documentation device having a digital video recorder directed towards the patient that records digital video images and audio signals concerning the care of the patient. An input interface is provided that accesses a library of patient care categories to select and output one or more patient care categories. A processor communicates with the digital video camera, audio recordings, and the input interface. A data storage device is in communication with the processor and digitally stores the digital video images, audio recordings, and the patient category output by the input interface. A date and time device communicates with the processor to provide a date and time marker correlating to the digital video images, audio recordings and the patient categories output by the input interface.

14 Claims, 6 Drawing Sheets

OTHER PUBLICATIONS

Intel, Field Study, "Mobile Clinical Assistant Platform Prototype" ElCamino Hospital, Feb. 2004.*

Webpage printout from www.viaproject.org/aboutus/press.asp dated Mar. 16, 2009 (1 page).

Webpage printout from http://weeklywire.com/ww/04-20-98/boston_feature_2.html dated Mar. 16, 2009 (4 pages).

Webpage printout from www.cmch.tv/research/fullrecord.asp?id=665 dated Mar. 16, 2009 (2 pages).

Email and search results from U.S. Patent Examiner Neal Sereboff, dated Jan. 27, 2009 (4 pages).

Email from VIA Analysis Coordinator dated Feb. 19, 2009 (3 pages).

* cited by examiner

US 7,555,437 B2

MEDICAL DOCUMENTATION SYSTEM

BACKGROUND OF THE INVENTION

This invention relates generally to a medical documentation system for documenting patient care substantially electronically to reduce the amount of data entry and paperwork required for such documentation.

Medical care includes doctors, nurses, and other healthcare providers documenting patient care through use of handwritten notes, forms, narratives, electronic data entry, etc. Such documents may require a considerable amount of time to produce.

Alternately, healthcare providers may dictate observations, instructions, and procedures either contemporaneously while examining or otherwise treating the patient, or, thereafter. These dictated observations must then be transcribed in some manner into usable written reports, computer files, or other documentation formats. Such reports may be for the patient's use, the writer's use, referral information, treatment histories, archival, and/or regulatory purposes.

Accordingly, it would be desirable to have a system which eliminates, or greatly reduces, the amount of data entry and paper-based documentation by healthcare providers and also to provide improved access to such documentation once created.

SUMMARY OF THE INVENTION

Generally, the present invention includes in one preferred embodiment an electronic documentation system for use in care of a patient by a health care provider, the system comprising a documentation device having a digital video recorder directed towards the patient that records digital video images of the care. A library of patient care categories is provided, and a manipulatable input interface is provided that accesses the library to select and output a patient care category from the library. A processor communicates with the digital video camera and the input interface and processes the digital video images, the patient care categories, and the output from the input interface. A data storage device stores the digital video images and the patient categories output by the input interface. A date and time stamp device communicates with the processor to provide a date and time marker associated with and/or correlating to the digital video images and the patient categories output by the input interface.

More specifically, the present invention additionally includes, in one preferred embodiment, a digital audio recorder that records digital audio. Also, a switch is provided that allows the patient and/or health care provider to selectively activate and deactivate the digital video camera and/or the audio recorder. An alarm generates an alert upon the switch being out of reach of the patient and/or the camera.

BRIEF DESCRIPTION OF THE DRAWINGS

The foregoing, as well as other objects of the present invention, will be further apparent from the following detailed description of the preferred embodiment of the invention, when taken together with the accompanying specification and the drawings, in which.

DESCRIPTION OF THE PREFERRED EMBODIMENT

Figure 1:
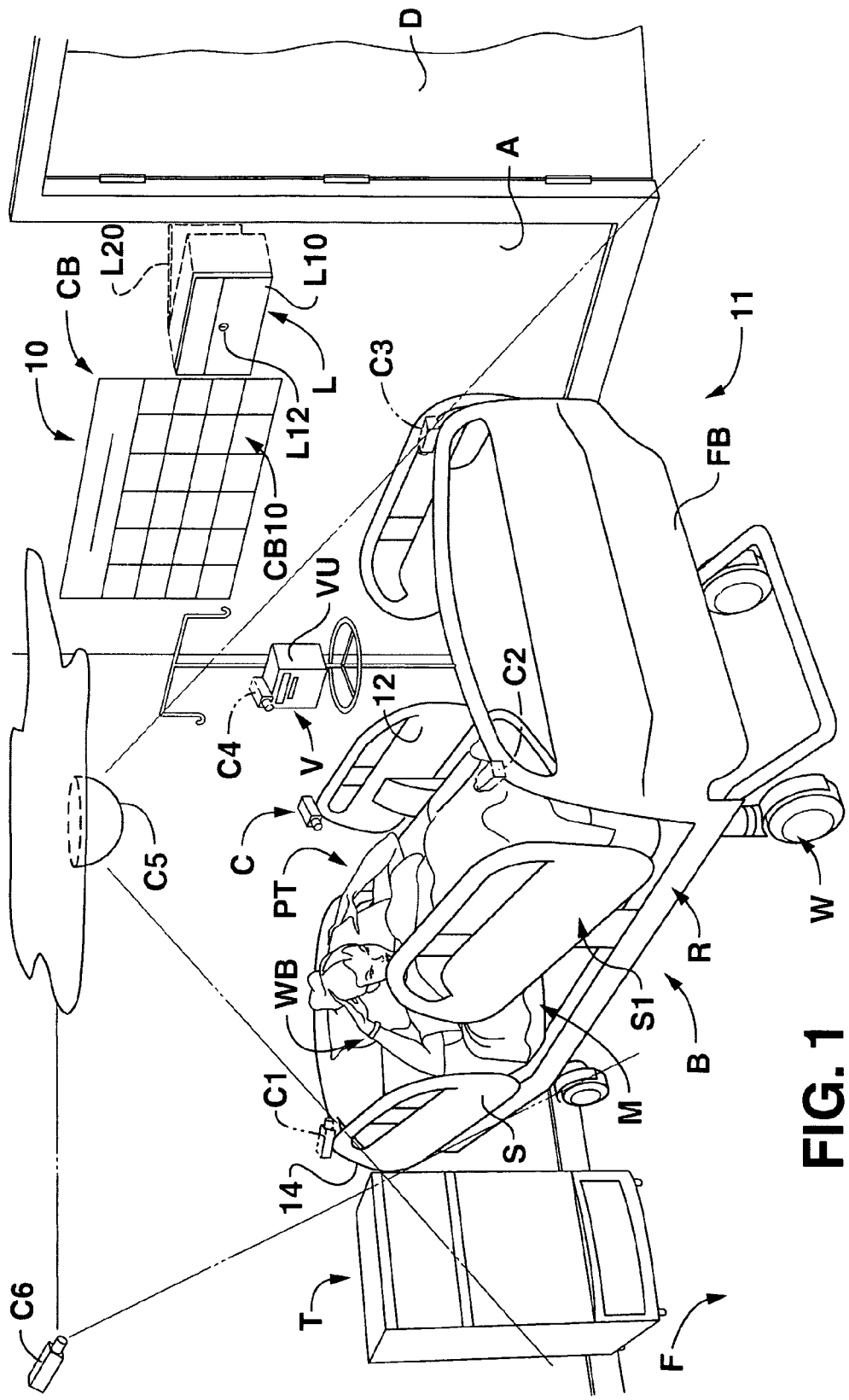
FIG. 1 is a perspective view of a medical documentation system constructed in accordance with the present invention.

The foregoing, as well as other objects of the present invention, will be further apparent from the following detailed description of the preferred embodiment of the invention, when taken together with the accompanying drawings and the description which follows set forth this invention in its preferred embodiment. However, it is contemplated that persons generally familiar with audio, video, and data recording and storage will be able to apply the novel characteristics of the structures illustrated and described herein in other contexts by modification of certain details. Accordingly, the drawings and description are not to be taken as restrictive on the scope of this invention, but are to be understood as broad and general teachings.

Referring now to the drawings in detail, wherein like reference characters represent like elements or features throughout the various views, the medical documentation system of the present invention is indicated generally in the figures by reference character 10.

Turning to FIG. 1 of the drawings, one preferred embodiment of medical documentation system 10 is illustrated. System 10 is shown located in an area, or room, generally 11, of a home or healthcare treatment facility, which could be a hospital room, having a bed, generally B, a bedside table, generally T, an intravenous (IV) device, generally V, having an IV device, generally IVU. Stand V can be of conventional design having rollers on the base thereof (not shown) for allowing stand V to be readily moved about the floor F.

Bed B is mounted on wheels, generally W, for allowing movement thereof and includes a frame, generally R, on which a mattress, generally M, is supported. A patient, generally PT, is shown on mattress M and is bounded by side rails, generally S and S1, and a footboard, generally FB, of bed B.

It is to be understood that the present invention may be used not only in traditional hospital and medical facility environments, but could also be used in other environments such as doctors' offices, the patient's home, during patient transport, etc.

A video, audio, and data collection, storage and documentation device, having a digital video recorder, referred to collectively herein as "camera," "camera unit," and/or "documentation device," generally C, constructed in accordance with the present invention, is shown positioned on side rail 12 of bed B. Data storage device, or camera unit, C is positioned such that it records video images of care provided patient PT, which may include images of patient PT and/or health care provider HCP, and also audio in the vicinity of patient PT and/or the health care provider. Such audio may be digitally recorded by camera C and may include the voice of patient PT, healthcare providers HCP (FIG. 4), and bystanders who may be nearby.

While in a preferred embodiment of the present invention only a single camera need be used, it is to be understood that additional cameras C1, C2, C3, C4, and C5, all shown in dotted lines in FIG. 1 could also be provided. It is also to be understood that a single camera could be used and placed at any one of the locations of cameras C1, C2, C3, C4, and C5, if desired. Camera C1 is shown connected to side rail 14, and cameras C2 and C3 are shown connected to footboard FB. Camera C4 is shown attached to stand V, and more particularly, attached to IV unit IVU. Camera C5 is attached to ceiling E and could include a wide angle and/or a fisheye lens and/or could be remotely controlled such that the direction viewed by camera C5 could be varied through use of a remote control unit.

Camera C6 is located in the upper corner of room 11. It is to be understood that although only one camera C is used in one preferred embodiment, one or more cameras could be used, and that such cameras could be positioned in a variety of locations, and the present invention is not to be limited to the positions and number of cameras shown in the drawings or otherwise disclosed herein.

System 10 also includes, in one preferred embodiment, a wristband, or a bracelet, generally WB, worn by patient PT. In one preferred embodiment, wristband WB is issued to the patient in lieu of, or in addition to, a patient identification bracelet. The operation wristband WB will be discussed in more detail below.

Medical documentation system 10 of also includes a lockable medication box, generally L, mounted in a wall A of the facility, shown in FIG. 1 as being adjacent door D. It is to be understood that medication box L could be positioned in locations other than disclosed herein without departing from the present invention. Medication box L extends through wall A into a room, hallway, compartment adjacent to room 11 and includes a compartment and a locking door L10 having a lock L12 therein. Door L10 is accessible within room 11 by a healthcare provider having access to lock 12. Box L also includes another door L20 (shown in dotted lines) accessible from a hallway, room, or other space adjacent room 11. Door L20 is also lockable and is accessible preferably by pharmacy personnel outside of the patient's room 11 for placing medications prescribed for patient PT within box L. Also, by allowing pharmacy personnel to restock the medications for patient PT from a hallway, for example, such pharmacy personnel are not only not required to enter the patient's room. Such direct placement of medications in a patient's room reduces the need for the patient's medications to be centrally stored and documented at a nurse's station, for example. Medication box L could be constructed of metal, wood, plastic, sheetrock, plaster, or a combination of the foregoing, with some other suitable material or material combination.

Medication box L can be used not only to store medications, but also documents, electronic storage media used by camera C, important papers, etc. Lock L12 could be a keyed lock, and/or could have a lock connected to a scanner or reader (not shown) and operated through use of a barcode, magnetic strip code, or biometric reader, such as a fingerprint reader, retina reader, hand vein pattern reader, etc. The lock (not shown) for door L20 could have a similar locking mechanism.

Medical documentation system 10 further includes, in one preferred embodiment, a communication board, generally CB, provided on wall A of room 11 of patient PT. Communication board CB is preferably a dry-erase type board, although it could be a chalkboard, corkboard, or some other suitable surface for storing information. Communication board could also be built-in, integral with and or applied to wall W, and could be painted, stenciled, a decal, a plastic sheet, etc., if desired. In one preferred embodiment, communication board CB has a grid, generally CB10, for allowing rows and columns of information to be entered concerning patient PT.

For example, grid CB10 of communication board CB may be used to list the patient's name and other patient information, such as demographics, history, and physical information. Additionally, it may include a listing of problems and plans and diagnosis and goals, assessment data, current highs and lows, vital signs and weight, etc. Further, communication board CB may include intervention information, such as current orders, their status, etc. Patient notifications, teaching information, and evaluations can also be provided on board CB, and board CB can be provided with pockets, sleeves, pouches, etc. (not shown) for receipt of actual paper documents such as doctor's orders, lab tests and results, medical and medication records, teaching handouts, discharge handouts, etc. Board CB may also include a portion on which questions for the healthcare provider can be written to further ensure that the patient PT and/or the friends, family, and/or designee of patient PT and/or their healthcare providers are reminded to ask such questions when the pertinent healthcare provider is available.

Additional information that can be provided on board CB may include family, friend, and/or designee contact phone numbers for patient PT, Health Insurance Portability and Accountability Act (HIPAA) clearance items, etc. The names and phone numbers of all treating physicians of patient PT can be written on board CB, as can also any allergies or precautions unique to patient PT. The board CB can be used to list all the disciplines involved in treating patient PT, such as physical therapy, occupational therapy, speech therapy, respiratory therapy, nutrition, social work, pastoral care, and any consults, such as surgeons, radiologists, anesthesiologists, other physicians consulted, etc. Moreover, the board CB can be used to list the predicted discharge date and/or the conditions which must be met before the patient PT will be discharged.

Communication board CB is, in one preferred embodiment, provided with grid CB10 pre-printed thereon with one or more of the above categories pre-printed thereon. Board CB can be color-coded for use only by selected personnel and/or for certain categories of information. For example, grid portions which are in a particular color, red for example, may only be written on and erased by a physician. It is to be understood, however, that a color other than red could be used for this purpose, with red only being discussed here for example purposes. Additionally, communication board CB could be videoed by a camera C at any given time, such that a video image data record could be made of the status of board CB.

Figure 2:
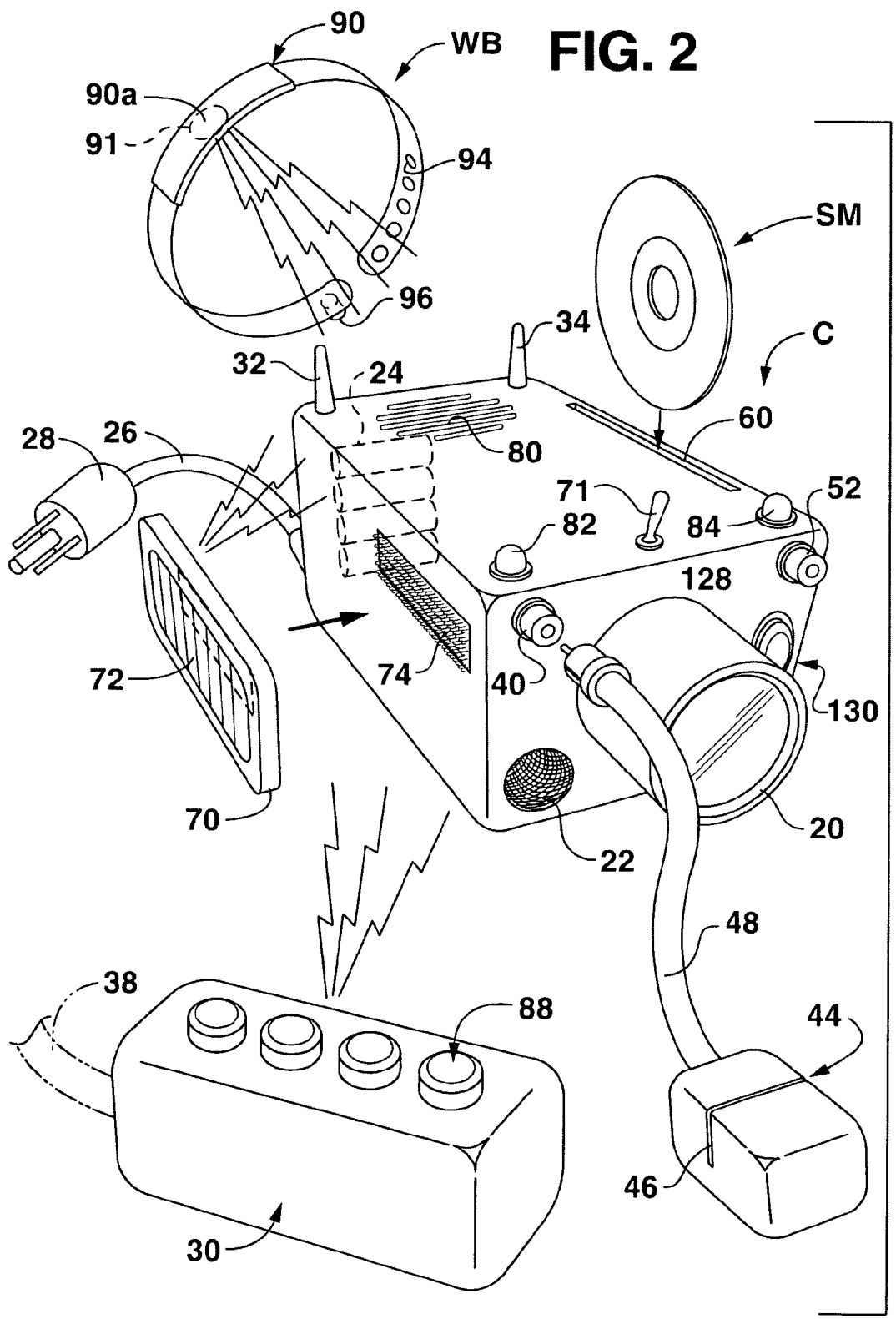
FIG. 2 is a perspective view of a video, sound, and data storage and documentation device constructed in accordance with the present invention having a data entry device and a patient wristband associated therewith.

FIG. 2 illustrates a video, audio, and data collection and documentation device, or, camera unit, C, which is preferably a digital camera having a digital processor and electronic storage capable of digitally storing video inputs received through camera lens 20 and for digitally storing audio inputs received through microphone 22. Camera unit C includes a battery pack 24, and may include, in one preferred embodiment, a power cord 26 for alternating current (AC) power having a plug 28. It is to be understood, however, that camera unit C could also receive and record analog video and audio inputs, if desired.

Preferably, camera unit C is of durable construction and suitable for repeated use by various healthcare providers, patients, etc. Also, camera unit C preferably includes an exterior that can be readily cleaned and sanitized to be suitable for hospital and medical facility cleanliness standards.

Camera C includes a control pendent, generally 30, which can be a wireless transmitter and/or receiver and/or transceiver communicating with camera unit C via receiving and transmitting antennae 32, 34 of camera C. Alternately, control pendent 30 can include a cable, generally 38, which is plugged into input 52 on camera C.

A scanner, or card reader, generally 44, having a card reader slot 46 could be provided which is connectable to camera C via a cable 48 in input 40 of camera C. Card reader 44 can be used to read magnetically encoded, bar-coded, holographically coded, electronically coded, optically coded cards, or cards or devices coded by other means to identify and validate a user in order to permit the user to operate camera C. Such a valid user could be a healthcare provider, a patient, and/or the patient's designee. Scanner 44 is preferably connected to a date/time stamp feature of camera C, discussed below, such that the time and date of use of camera C, and the identity of the user, is stored in camera C. Such time and date formation can, if desired, be polled or interrogated to determine who activated camera C and when, as well as what event, such as a treatment, took place at that time. Scanner 44 could also include a wireless feature which would Camera C includes a receptacle, or slot, 60 for receipt of an electronic storage media device, generally SM, such as a compact disc (CD), digital video disc (DVD), mini DVD, memory card, memory cassette, flash drive, vault, etc., for storing digital data created by camera C. Such digital data could include video images as input from lens 20, digital audio signals as input from microphone 22, input from card reader input from reader 44, input from control input from pendent 30, input from bracelet WB, and/or input from a data entry device, such as a touchpad data entry and an input interface, or storage device, 70 manipulatable by the patient and/or the healthcare provider.

Data entry and storage device 70 has a switch, generally 71, manipulatable by the patient and/or a healthcare provider, and/or a touch screen, generally 72, for activation of camera C for video recording, sound recording, and for entering in data, such as treatment codes, diagnosis codes, patient information, vital signs, medications, and other information. Device 70 can be attached to camera C, for example through use of releasable fastening means such as Velcro® 74, snaps, clips, buckles, magnets (none shown), or some other fastener, or could be attached to camera C, if desired. Device 70 could also be used as a video playback device, with screen 72 being a liquid crystal display (LCD) screen, or some other type of display, for displaying video inputs received through lens 20 on a real-time basis and/or on a recorded basis. Device 70 could be linked to camera C to receive such information wirelessly, for example through a Wi-Fi, Bluetooth, or some other wireless connection, or could be hardwired to camera C, if desired. Camera C could also be used to play back audio recordings real-time and/or on a recorded basis through a speaker 80, if desired. Additional sound and video input and output jacks (not shown) could also be provided on camera C, if desired.

Camera C preferably includes at least one indicator light, which could be an incandescent bulb, a light emitting diode (LED), or some other illumination device, generally 82, that glows steadily and/or intermittently when camera C is in operation recording video and/or sound images. Light 82 could also indicate when camera C has its power on. For example, when camera C is powered up, but not recording, light 82 could flash intermittently, and when recording, light 82 could be steadily illuminated. It is to be understood that additional specific lights could also be used for representing different statuses of camera C, such as power on, audio recording, video recording, data entry recording from devices 10, 120, etc., if desired.

Camera C may also emit a continuous and/or intermittent tone through speaker 80 when in operation. In one preferred embodiment, speaker 80 emits a distinctive tone when the video recording and/or the sound recording feature of camera C are initially activated and another distinctive tone when such features are subsequently deactivated. Such distinctive tones would be of a quality and/or type to clearly alert the patient, the healthcare provider, and anyone else in the vicinity that camera C was being activated or deactivated. During activation, however, the patient and/or health care provider, and/or other bystanders would be videoed and their sounds recorded. In a preferred embodiment, speaker 80 could be quiet or altogether silent.

Camera C may include another indicator light or LED 84 which is illuminated continuously and/or intermittently in the event an alarm condition exists with camera C. For example, should patient PT be further than a predetermined distance from the switch 71 of camera C, such as beyond arm's length or reach of camera C or other activation/deactivation control of camera C, indicator light 84 would become lit. Additionally, or instead of indicator light 84 becoming lit in an alarm condition, speaker 80 could also emit a predetermined continuous and/or intermittent sound notifying those nearby that patient PT is beyond a predetermined distance from control of camera C. In one preferred embodiment, when an alarm condition occurs, not only would camera C give visual alerts using light 84 and/or speaker 80, but camera C would also alert the attending nurses' station for assistance. In one preferred embodiment, camera C would operate in a passive mode, wherein no video images or audio signals are recorded, but nonetheless camera C continues to sense whether patient PT is within a predetermined distance from the switch 71 of camera C, such as within arm's length or reach of camera C or other activation/deactivation control of camera C. If such predetermined distance is exceeded, then an alarm would be generated.

Further, in the event patient PT has an emergency or is in distress, patient PT can push a button, generally 88, on control pendent 30 and/or a data entry device as discussed above to sound the alarm through speaker 80. Additionally, patient PT could use wristband WB for placing camera C in the alarm condition, thereby illuminating light 84 and sounding speaker 80.

Wristband WB includes a remote actuator, which could be a transmitter and/or transceiver, generally 90, attached to a band 92, which is adjustable to fit the size of the wrist of a patient. Band 92 includes adjustment openings 94 which are received by a fastener, generally 96, for attachment of band 92 about the patient's wrist. Transceiver 90 can itself include an audible alarm which sounds should the patient go beyond a predetermined distance from camera C, i.e., a distance out of view of lens 20 of camera C, or further than a preset distance from camera C. Transceiver 90 can also be used to activate and deactivate camera C and/or to place camera C in an alarm condition by patient PT squeezing or depressing a predetermined portion 90a of transceiver 90 for at least a predetermined period of time. In this event, an alarm signal is sent to camera C in order to put camera C in an alarm condition.

Wristband WB could incorporate in one preferred embodiment a marker surface and/or device (such as a reflector, and infrared emitter, a light source of a predetermined wavelength, etc.) detectable by the lens of camera C, that, when in the field of view of and sensed/viewed by the lens of camera C, gives and indication that patient PT is also within view of camera C. If such marker or device is not "seen" by lens 20, then an alarm would be generated.

System 10 includes the capability to generate an alarm in the event wristband WB moves beyond a predetermined distance from camera C, which could indicate that the patient is out of reach of the camera C and thus cannot operate camera-mounted activation switch 71 and/or a data entry device 70, 120, to control camera C. It should be noted that a healthcare provider can also activate camera C, when necessary.

While a variety of means could be used to monitor the distance relationship of wristband WB to camera C, one system could include wristband WB having a radio frequency identification device (RFDI), generally 91, and camera C may interrogate device 91 periodically to determine whether wristband WB is still within a predetermined distance from camera C. Such predetermined distance may, in one preferred embodiment, be the approximate arm's length of the patient's arm to ensure the patient remains within reach of camera C. Preferably, camera C is powered up substantially full time, around-the-clock upon being assigned to the patient, even when camera C is not being used to record video, sound or data, in order that the distance limit of wristband WB with respect to camera C can be continuously monitored.

While a wristband WB has been shown in the drawings as including devices for operation of camera C, it is to be understood that such devices could be in other forms other than wristband WB, and could be, for example, identification tags, key fobs, handheld controllers, ankle bracelets, necklaces, keys, etc., if desired.

Figure 3:
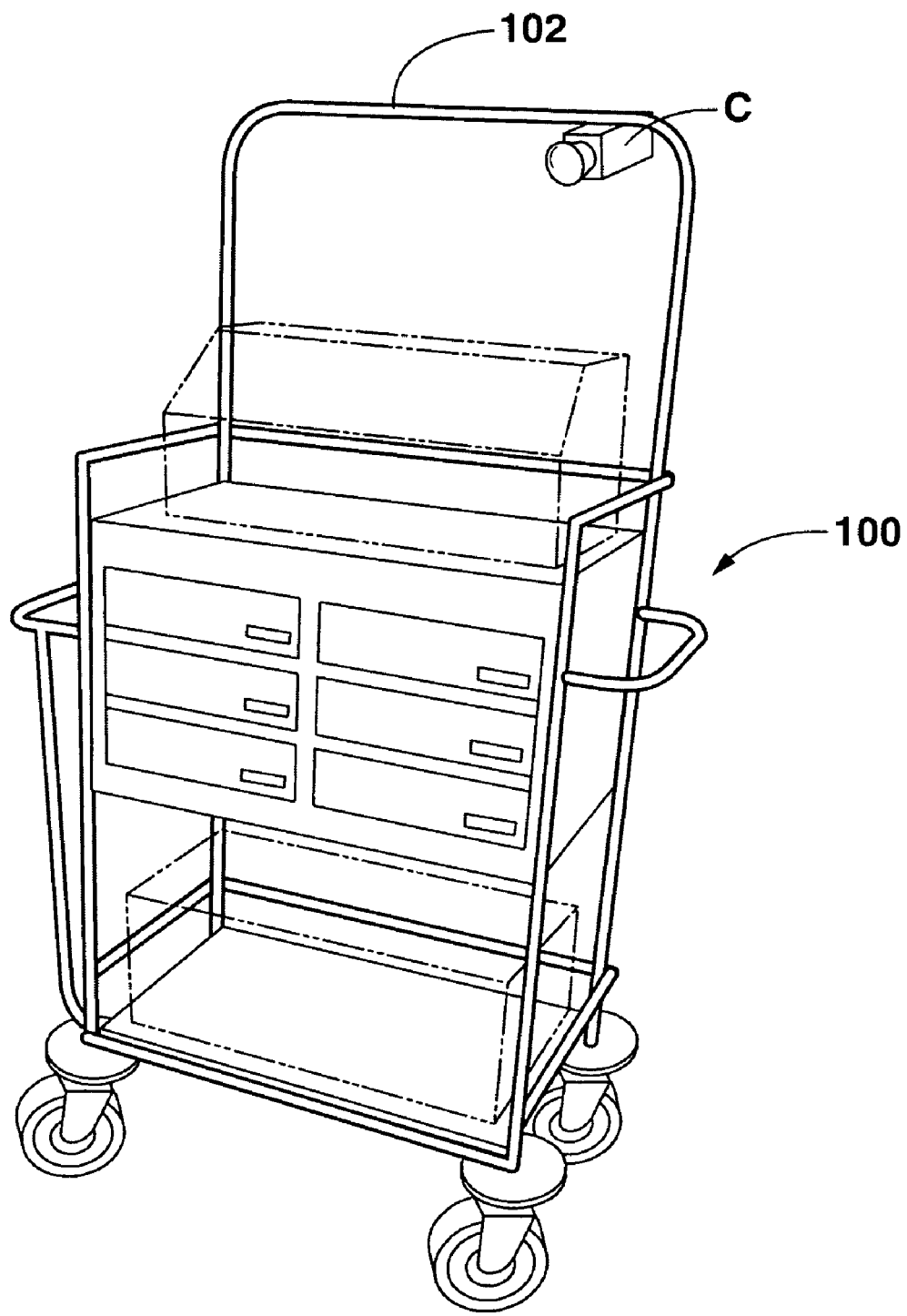
FIG. 3 is a perspective view of a cart, such as a crash cart, having a storage device such as illustrated in FIG. 2.

FIG. 3 illustrates a cart, generally 100, such as of the type typically used in hospitals, doctor's offices, and other healthcare facilities. A camera C is attached to an upper portion, generally 102, of cart 100, with cart 100 providing another location on which camera C may be mounted for recording video images of patient PT and also for recording audio inputs. Because cart 100 is movable about floor F, the field of view of camera C attached thereto can be easily changed simply by moving cart 100.

Figure 4:
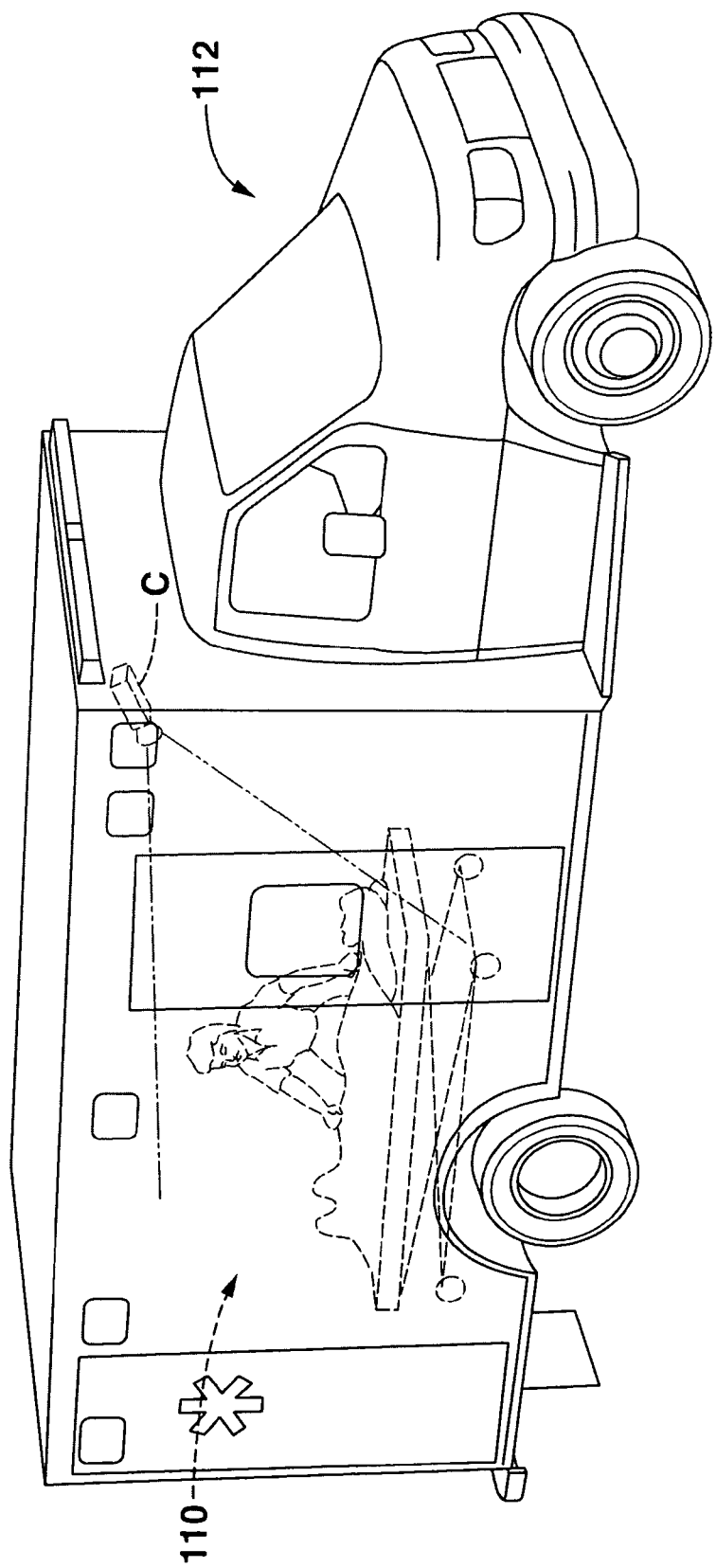
FIG. 4 is a perspective view of an ambulance having a patient compartment provided with a data storage and documentation device such as shown in FIG. 2.

FIG. 4 illustrates another embodiment in which camera unit C can be used. In this embodiment, camera unit C is illustrated being used within a patient compartment, generally 110, of an ambulance, generally 112, and is positioned for viewing the healthcare services provided by healthcare provider HCP as patient PT is supported on a stretcher, gurney, or other patient transport device, generally 114.

In one preferred embodiment, camera C attached to cart 100 and used in patient compartment 110 includes a wide angle and/or a fish eye lens for an increased filed of view for camera C. Additionally, such a wide angle and/or a fish eye lens could also be used when camera C is used for documentation of a relatively large space, such as an entire room, operating room, etc. for simultaneously recording numerous medical care actions.

Figure 5:
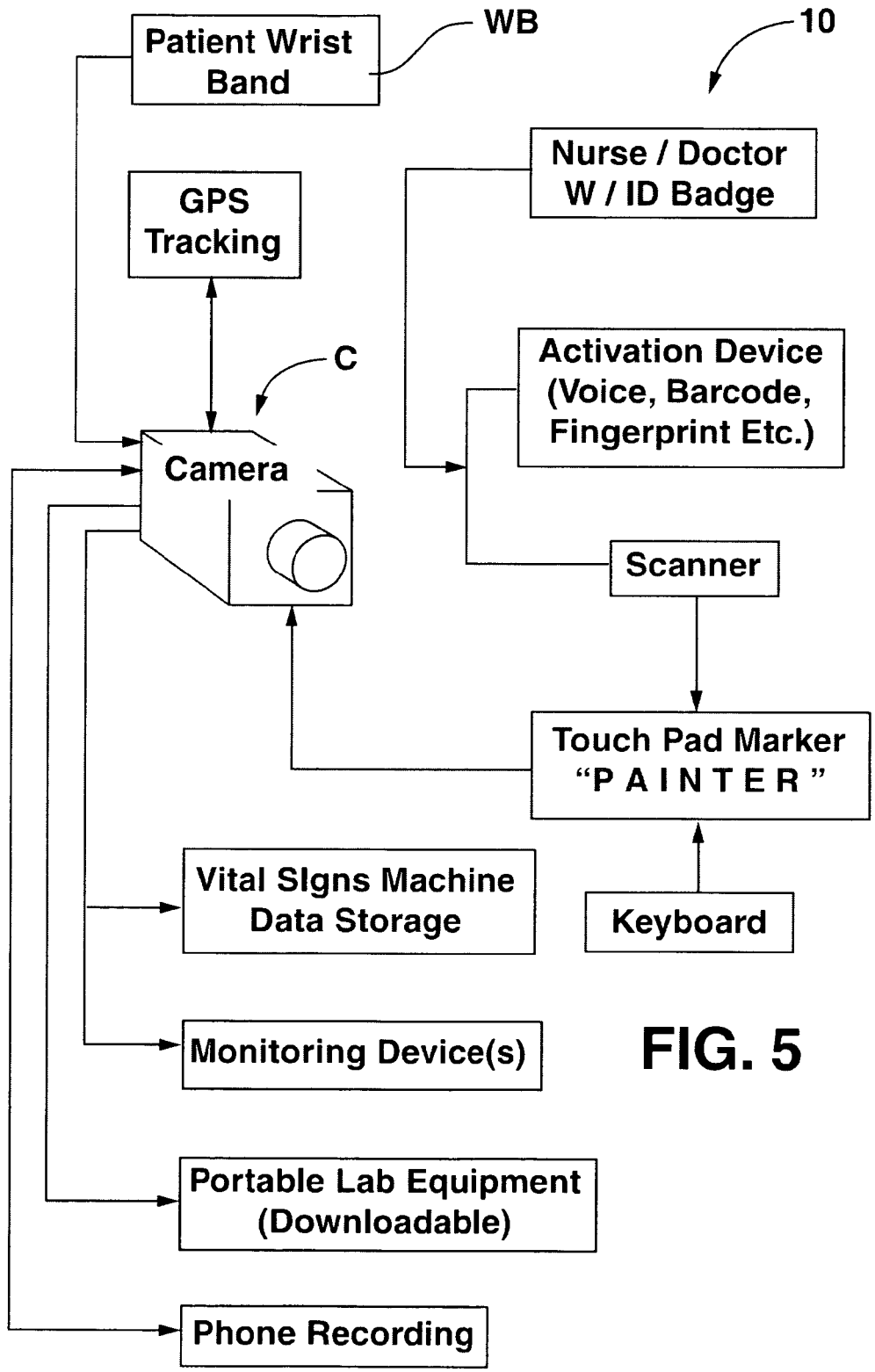
FIG. 5 is a functional diagram illustrating the medical documentation system of the present invention.

FIG. 5 illustrates a preferred embodiment of a medical documentation system 10 constructed in accordance with the present invention, wherein camera unit C is integrated into the provision of healthcare services for a patient PT. Camera unit C, as discussed above, includes a transceiver function for receiving and/or transmitting information to wristband WVB and/or data entry device 70. Additionally, camera unit C may include, in one preferred embodiment, a global positioning system (GPS) capability for allowing the location of camera unit C, and therefore patient PT also, to be tracked, if desired. Antennae 32, 34 of camera C can be used in performing a GPS transceiver function. One or more inputs, 40, 52 could be provided, in addition to other inputs (not shown) wherein data from medical measurement devices for measuring physical characteristics and/or conditions of a patient, such as vital sign devices, such as blood pressure machines, temperature reading devices, respiratory devices, blood oxygen level devices, EKG devices, and other devices, can be connected and information transferred to and from such devices and camera C. For example, information from portable lab equipment and/or information stored or otherwise collected from camera unit C can be downloaded to such portable lab equipment. Camera C could also be used to access and/or sort information from such medical measurement devices on a real-time and/or recorded basis based on the patient care category type library of procedures and measurements or other data stored on camera C. A library of patient care category types would be provided in camera C and could include the type of objective numerical data, condition or measurement taken, i.e., vital sign measurements, EKG measurements, blood oxygen levels, etc.), the type of device (or the healthcare provider) taking the measurement, the date and time the measurement was taken, etc. The patient care categories could also include the food intake of the patient.

Camera unit C could also include a phone and/or modem for making calls wirelessly and/or through wired connections. Phone call made using camera C could be recorded as data and stored by camera C. Such phone calls could be, for example, nurses' calls to physicians for patient instructions.

Camera C can also include an automatic telephone dialer to automatically generate phone calls to predetermined numbers in the event of an alarm condition, notifying the phone or other device (or the nurses' station) of the particular alarm condition, or otherwise call such number with information in some other event. Further, camera C could be configured to include a modem for receiving phone calls such that the operation of camera C could be remotely accessed and/or modified by a caller, such as a doctor, dialing the phone number of such camera C and entering in a predetermined code for changing the mode of operation of camera C or for querying or polling camera C to receive desired information. This would allow an authorized healthcare provider to remotely check the status of a patient's condition by phone.

Camera C could also be connectable to the internet, such as through a wired or wireless connection (such as Wi-Fi, Bluetooth, etc.) such that camera C could be accessed and controlled via internet connection and could, if desired, act as a webcam for use by an authorized user.

Figure 6:
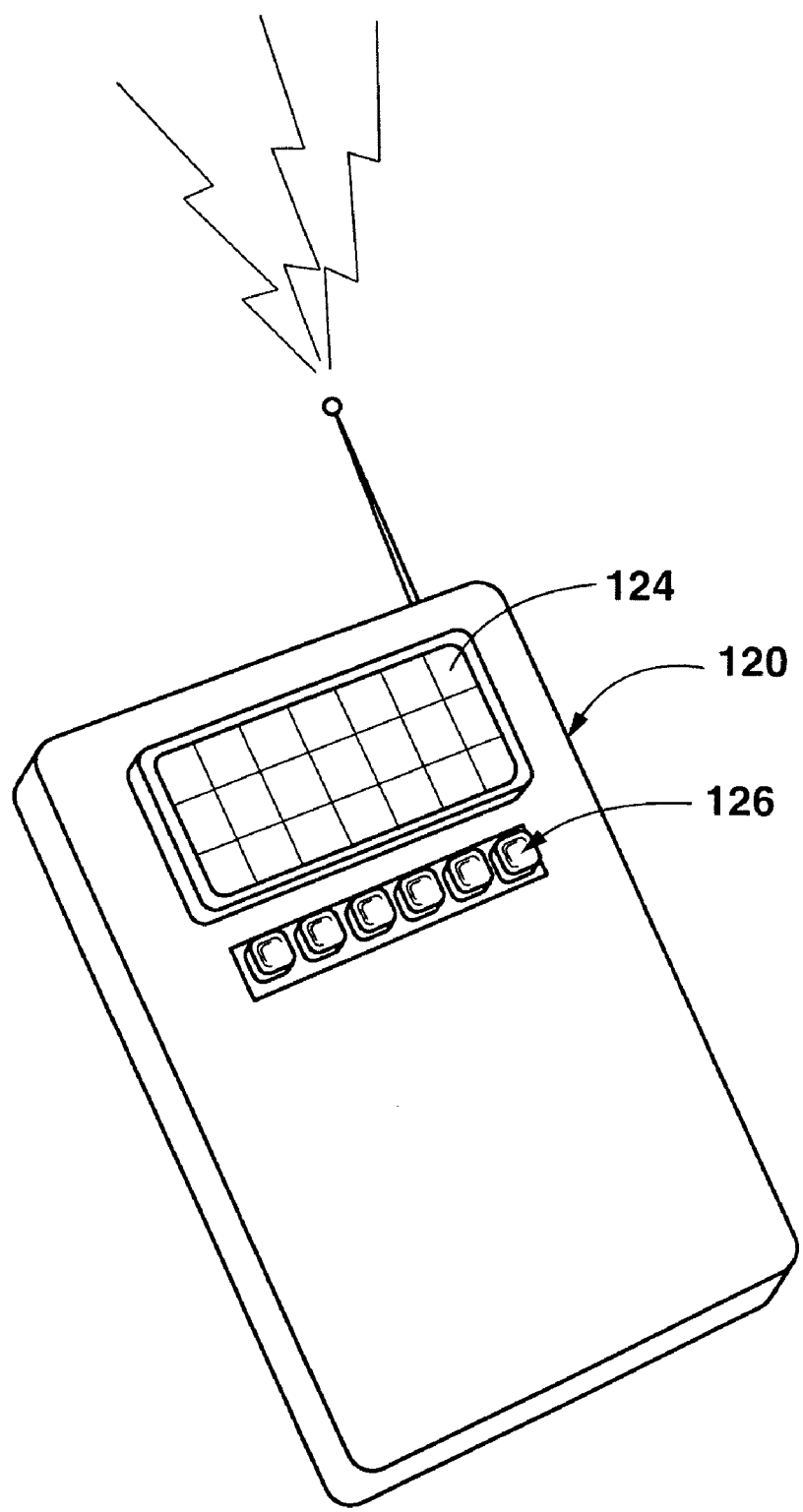
FIG. 6 is a perspective view of a data collection device for collecting and processing information concerning a patient and usable in association with the data storage and documentation device shown in FIG. 2.

FIG. 5 also illustrates operation of touchpad data entry device 70 and/or an input interface, or storage device, 120 manipulatable by the patient and/or the healthcare provider. Data entry device 120 is illustrated in FIG. 6. In one preferred embodiment, before data can be entered into devices 70 or 120, the user is authenticated. For example, a nurse, doctor, or other healthcare provider may be required to have an ID badge, card, key fob, or other device with a barcode, magnetic strip, electronic chip, optical configuration, etc., recognizable by scanner 44 for identifying and authenticating such user. Other authentication means could be the user's voice, when matched with a recorded voice print stored or accessible by camera C, and/or biometric identifiers, such as fingerprint, retina scan, hand vein map information, etc. for use of scanner 44.

Once identified and authenticated, the user could use device 70 and/or device 120 for entering data to be stored thereon and/or on camera unit C. Note device 120 includes a screen 124, which could be an LCD screen, plasma screen or otherwise and which could be touch sensitive for allowing a user to enter data through their finger(s), a stylus (not shown), or otherwise. Alternately, a keyboard (FIG. 5) could be included for entering data into device 70 and/or device 120. Device 120 may also include other controls, generally 126, for controlling operation of device 120, such as, for example, the remote control of camera C5 (FIG. 1), discussed above, power for camera C and/or device 120, etc.

Scanner 44 of camera unit C may also include a scanner, such as a barcode scanner, infrared scanner, electronic scanner, or other scanner, generally 130, for scanning medication and/or supplies dispensed to patient PT. This reading of medication could be correlated with doctor's orders medication data entered and stored on camera C by a healthcare provider in order to record all medications given and to insure the proper medication is given patient PT, per the doctor's orders earlier entered into camera C. Supplies used in the care of the patient can also be recorded via scanner 130 and tracked. Scanner 44 is preferably connected to a date/time stamp feature of camera C, discussed below, such that the time and date of use of camera C, and the medications and/or supplies dispensed, etc. are stored in camera C In use, a healthcare provider is identified and authenticated through use scanner 44 and an identification badge, identification card, electronic device (such as are used in fast-pay applications where such devices are simply waived in front of a reader), an RFID device, and/or through biometric means such as fingerprint, etc. Once authenticated, touchpad device 70 and/or 120 can be used for entering task/procedure categories involving treatment of the patient. For example, a nurse may perform a "P-A-I-N-T-E-R" analysis of the patient, "PAINTER" being an acronym for: plan, assess, intervene, notify, teach, evaluate, and record, which are steps followed in examining, treating, and caring for a patient. Similarly, such patient treatment could involve steps represented by another acronym, "A-D-P-I-E," for: assess, diagnose, plan, intervene, and evaluate. Also, either the healthcare provider or patient PT could activate camera unit C to begin audio and video recording of the healthcare provider's visit and/or examination of patient PT.

Camera unit C includes a calendar and clock feature having date-time stamp, or marker, capabilities such that upon activation of camera C, a date-time stamp entry is made and recorded on the electronic storage device SM which, as noted above, could be a CD, DVD, card, disk, etc. The storage media SM is preferably a universal-type storage media such that the information stored thereon, i.e., the patient's data, video, and audio documentation, can be easily disseminated to other healthcare providers at other medical facilities. Preferably, the treatment/observation task/procedure categories entered on a touchpad 70, 120, and information concerning the patient's vital signs, as received from monitors connected to camera C or as otherwise taken by provider HCP are simultaneously stored by camera C on storage media SM and/or on memory internal to camera C. Such vital or other signs can be input verbally and recorded by camera C and/or entered into device 70 or 120 and stored by camera C. It is also to be understood that camera C could operate 24 hours a day, seven days a week as a data recording device, even in those times when the audio and video recording functions of camera C are not being used.

The processor in camera C is interconnected with the video input from lens 20, scanner 44, the audio input from microphone 22, data entry devices 70, 120, and the calendar and clock feature of camera C to allow a date-time stamp to be associated with each input from the lens 20, scanner 44, microphone 22, and devices 70, 120. Camera C is configured to allow processor to be polled or interrogated to determine what inputs were made at a selected time and date and/or to determine when a selected input was made to camera C.

For example, in a patient visit, healthcare provider HCP may, using a touchpad 70, 120, indicate that the patient was given medication, had their vital signs taken, had a wound dressed, was fed, etc. By indexing these differing types of care categories using device 70 and/or 120, the storage media SM, which preferably stores such categories with one or more classification identifiers, allows the storage media SM to later be quickly scanned and/or sorted for particular classification identifiers to isolate particular care categories and/or classifications. Also, such data is configured to be readily extracted and printed out as a paper record, to a computer, the computer having conventional software.

Preferably, a single camera unit C is used with a patient PT, although multiple camera units can be used and could be mounted to the patient's bed or to a moveable device, such as stand V, so that the camera would move with the patient when the patient leaves his or her bed, such as when ambulating down a hall.

The patient and health care providers would preferably be in control of the camera C, and could switch it on or switch it off as desired using wristband an auxiliary switch on WB, pendant 30 and/or devices 70, 120. There may be certain concerns, such as privacy concerns, wherein the patient would not want the camera to be on, and thus the patient would preferably maintain control of the camera's operation. Preferably, when the video and/or audio recording features of the camera are activated, as noted above, camera C emits a tone and/or illuminates a light 82 alerting those nearby that camera C is operational.

In an example application of system 10, camera C could be used by a nurse, for example, when using supplies with a patient and/or in medicating the patient, such as in the giving of a pill to a patient. Camera C can include a code reader, such as a barcode reader, generally 128, for scanning a barcode, or other coding, on the pill's packaging or container. This code would then be compared with the memory of camera C to insure it correlates with medication prescribed by the doctor. Also, the nurse could hold the pill in front of the camera lens 20 so that camera C could record the image of the type of pill being administered. Additionally, the nurse could verbally state for microphone 22 of the camera what type of medication the pill was in order to record the type of pill being administered. Camera C would include a date-time stamp recording of this administration of the pill and would also include care category/type stamps, i.e., classification identifiers, for each such recorded event. If medical supplies were also being used, the barcode or other code on the supplies or their packaging could be scanned by camera C, and/or verbally stated for microphone 22, and such data stored in the memory of camera C for billing purposes or otherwise.

In one preferred embodiment, a patient PT would be issued their own camera C upon being admitted to the hospital to be used as they chose during their entire hospital stay. Thus, the patient could selectively activate camera C and control its use.

In an additional embodiment of the present invention, a camera C could be used by healthcare providers themselves. Camera C would operate in a similar manner as discussed above, with the healthcare provider being in control of the operation of camera C, so that a healthcare provider could record with both video and audio treatments and patient care, as desired. This could reduce the burden of data entry and paperwork on the healthcare provider, in that a digital record is maintained through use of camera C. Additionally, it is anticipated that use of camera C in this manner could free the healthcare provider to spend more time in performing patient care in discussions with the patient, etc., rather than using time to document the care.

Instead of, or in addition to, the phone connection discussed above, camera C could also have an automatic messaging device having the ability to automatically send emails, text messages, etc., during an alarm condition, or as otherwise desired, such as when a certain event occurs (i.e., a patient's temperature, blood pressure, respiratory rate rises above or below a preset number, etc.), to the healthcare provider alerting of such alarm or event. For example, the emails could be sent to the personal digital assistant (PDA) of the healthcare provider, such as the healthcare provider's cell phone (via text messaging), Blackberry®, Palm®, or other similar type of device. This transmission of emails and/or text messaging by camera C could be done through a wired system and/or through a Wi-Fi, Bluetooth, or other wireless communication system. Similarly, a healthcare provider could send email instructions to camera C, or instructions via some other data communication protocol, for polling, interrogating, querying, or for changing the operation limits and/or parameters, etc. of camera C.

Camera C may also include a motion sensor, or detector. Sensor 130 could also be used for such motion detection, and camera C could be configured such that it becomes activated and remains activate so long as it senses motion within the field of view of sensor 130 and for a predetermined period of time after such motion stops. This will allow for camera C to operate on an automatic basis to record video and/or audio inputs so long as sensor 130 detects motion (and for a time thereafter, if desired) of patient PT, healthcare provider HCP, or other persons or items.

Also, camera C could include an infrared device, which could include sensor 130, which would detect the patient. In the event the patient is no longer sensed by camera C, this could be an indication that lens 20 of camera C is no longer directed at the patient, i.e., the patient is not within the view of camera C, and the infrared device could then put camera C in an alarm condition to immediately, or after a predetermined period of time, alert the patient and others that the patient is not within the field of view of lens 20 of camera C.

In a further embodiment, sensor 130 could be more refined to actually store and recognize a unique infrared signature for patient PT and could thus differentiate patient PR from other people who may be in the room. Thus, even if sensor 130 sensed that a person was within the field of view of lens 20, an alarm would be initiated if the infrared signature of that person did not match the infrared image of the patient PT.

From the foregoing, it can be seen that the medical documentation system of the present invention electronically documents patient care through digital video images, digital audio images, and diagnosis, treatment and observation data input on a date-time marked basis which can be recalled on the basis of objective data, time, event, task, healthcare provider, vital sign, and other medical condition of the patient. Camera C can be activated by patient PT, a health care provider HCP and/or activated by another event, such as upon movement of a comatose patient though use of motion detector 130, upon receipt of information by camera C from a sensor that the patient is not experiencing a normal sinus rhythm, etc.

While preferred embodiments of the invention have been described using specific terms, such description is for present illustrative purposes only, and it is to be understood that changes and variations to such embodiments, including but not limited to the substitution of equivalent features or parts, and the reversal of various features thereof, may be practiced by those of ordinary skill in the art without departing from the spirit or scope of the following claims.

What is claimed is:

1. A method for video documentation of health care of a patient, the method comprising:
   initiating the health care of said patient by a health care provider;
   establishing a computer-based health care record for said patient;
   generally concurrently with said initiation of said health care, said health care provider issuing to said patient a video camera configured for use by said patient and for use by said health care provider to video document said health care of said patient, wherein said video documentation from said issued video camera is added to said computer-based health care record; said video camera including an electronic library of patient care categories and a user input interface for allowing selection of at least one of said patient care categories;
   setting using at least one processor device a predetermined distance between said patient and said video camera;
   connecting a monitoring device to said patient;
   associating using said at least one processor device and a wireless electronic connection said video camera and said monitoring device;
   monitoring using said at least one processor device the distance between said video camera and said patient;
   generating an alert using said at least one processor device and an alarm device in the event said video camera is beyond said predetermined distance from said patient;
   maintaining said connection of said monitoring device to said patient for substantially the duration of said health care of said patient;
   selecting a patient care category from said electronic library of patient care categories using said user input interface;
   video documenting said health care of said patient using said video camera;
   associating said video documentation with said selected patient care category using said user input interface; and
   updating said video documentation of said health care to said computer-based health care record of said patient.

2. The method as defined in claim 1, further comprising:
   providing a remote control actuator that allows the patient to selectively remotely activate and deactivate said video camera; and
   issuing said remote control actuator to the possession of said patient generally concurrently with said issuing of said video camera to the possession of said patient.

3. The method as defined in claim 1, further comprising:
   recalling said video documentation associated with said selected patient care category using said user input interface.

4. The method as defined in claim 1, further comprising:
   said an electronic library of patient care categories including medical interventions, patient teachings, patient treatment codes, patient diagnosis codes, patient medications, and billing information;
   recalling said video documentation associated with said selected patient care category using said user input interface.

5. The method as defined in claim 1, further comprising:
   said health care provider performing said use of said video camera to video document said health care of said patient;
   said health care provider selecting said at least one patient care category from said electronic library of patient care categories using said user input interface;

recalling said video documentation associated with said selected patient care category using said user input interface.

6. The method as defined in claim 1, further comprising:
said patient performing said use of said video camera to video document said health care of said patient;
recalling said video documentation associated with said selected patient care category using said user input interface.

7. The method as defined in claim 1, wherein said monitoring device is connected to a wristband wearable by said patient.

8. The method as defined in claim 1, wherein said predetermined distance is approximately the arm's reach distance of the patient.

9. The method as defined in claim 1, wherein said alarm is attached to said monitoring device.

10. The method as defined in claim 1, wherein said alarm is attached to said video camera.

11. The method as defined in claim 1, wherein said issuing of said video camera to the possession of said patient is done substantially concurrently with said connecting of said monitoring device to said patient.

12. The method as defined in claim 1, wherein said electronic library of patient care categories includes medical interventions, patient teachings, patient treatment codes, patient diagnosis codes, patient medications, and billing information.

13. The method as defined in claim 1, wherein said monitoring device includes a remote control actuator that allows the patient to selectively remotely generate said alert and to selectively remotely activate and deactivate said video camera.

14. A method for video documentation of health care of a patient, the method comprising:
initiating the health care of said patient by a health care provider;
establishing a computer-based health care record for said patient;
generally concurrently with said initiation of said health care, said health care provider issuing to said patient a video camera configured for use by said patient and for use by said health care provider to video document said health care of said patient, wherein said video documentation from said issued video camera is added to said computer-based health care record; said video camera including an electronic library of patient care categories and a user input interface for allowing selection of at least one of said patient care categories;
setting using at least one processor device a predetermined distance between said patient and said video camera;
connecting a monitoring device to said patient;
associating using said at least one processor device and a wireless electronic connection said video camera and said monitoring device;
monitoring using said at least one processor device the distance between said video camera and said patient;
generating an alert using said at least one processor device and an alarm device in the event said video camera is beyond said predetermined distance from said patient;
maintaining said connection of said monitoring device to said patient for substantially the duration of said health care of said patient;
said health care provider selecting a patient care category from said electronic library of patient care categories using said user input interface;
at least one of said patient and said health care provider video documenting said health care of said patient using said video camera;
associating said video documentation with said selected patient care category using said user input interface;
updating said video documentation of said health care to said computer-based health care record of said patient; and
recalling said video documentation associated with said selected patient care category using said user input interface.

* * * * *